United States Patent [19]

Efner

[11] Patent Number: 4,923,643
[45] Date of Patent: May 8, 1990

[54] ANTIMONY MERCAPTIDE ESTERS AND METHODS OF PREPARING THE SAME

[75] Inventor: Howard F. Efner, Bartlesville, Okla.

[73] Assignee: Phillips Petroleum Company, Bartlesville, Okla.

[21] Appl. No.: 245,784

[22] Filed: Sep. 16, 1988

[51] Int. Cl.$^5$ .............................. C07F 9/90; C07F 9/92; C11C 3/02; C08H 3/00

[52] U.S. Cl. .............................................. 260/410.9 R

[58] Field of Search ............... 556/77; 260/399, 410.5, 260/410.9 R

[56] References Cited

U.S. PATENT DOCUMENTS

| | | | |
|---|---|---|---|
| 3,530,158 | 9/1970 | Leebrick et al. | 260/446 |
| 3,887,508 | 6/1975 | Dieckmann | 260/23 XA |
| 4,029,618 | 6/1977 | Dieckmann | 260/23 XA |
| 4,158,640 | 6/1979 | Dieckmann | 252/400 R |
| 4,336,168 | 6/1988 | Hoch et al. | 556/77 |
| 4,396,552 | 8/1983 | Knobloch et al. | 556/77 |
| 4,615,836 | 10/1986 | Bobsein | 260/399 |

Primary Examiner—Paul F. Shaver
Attorney, Agent, or Firm—Laney, Dougherty, Hessin & Beavers

[57] ABSTRACT

Antimony mercaptide esters of the formula

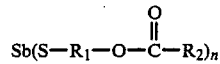

are provided. The preparation of such esters comprises reacting an antimony oxide compound with a mercapto alcohol in a first reaction to form an antimony mercaptide intermediate. The intermediate is then reacted with an organic acid or the anhydride thereof in a second reaction to form the antimony mercaptide ester.

25 Claims, No Drawings

ANTIMONY MERCAPTIDE ESTERS AND METHODS OF PREPARING THE SAME

BACKGROUND OF THE INVENTION

1. Field of the Invention

The present invention relates to novel antimony mercaptide esters of the formula

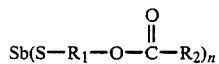
$$Sb(S-R_1-O-\overset{\overset{O}{\|}}{C}-R_2)_n$$

and methods of preparing such esters.

2. Description of the Prior Art

Antimony mercaptoacid esters of the formula

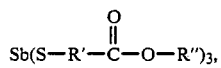
$$Sb(S-R'-\overset{\overset{O}{\|}}{C}-O-R'')_3,$$

wherein R' and R'' represent alkylene, arylene, alkarylene, or aralkylene groups have been prepared and used heretofore. For example, U.S. Pat. No. 4,336,168 issued Jan. 22, 1982, discloses such antimony mercaptoacid esters and their preparation by reacting a thioester with an antimony oxide compound. The reaction is illustrated in Example 1 of the patent wherein isooctyl thioglycolate is shown to have been reacted with antimony oxide to form antimony tris-(isooctyl thioglycolate) of the formula

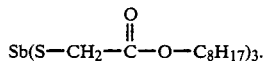
$$Sb(S-CH_2-\overset{\overset{O}{\|}}{C}-O-C_8H_{17})_3.$$

Thioesters of the formula

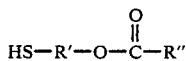
$$HS-R'-O-\overset{\overset{O}{\|}}{C}-R''$$

have heretofore been prepared by reacting an organic carboxylic acid with a mercapto alcohol in the presence of an esterification catalyst. However, such reactions often produce a number of undesirable byproducts such as thioxane and insoluble polymers of the mercapto alcohol. While special catalysts have been developed and used, they often require highly elevated temperatures and extended reaction times.

By the present invention, novel antimony mercaptide esters are provided as well as methods of preparing the esters whereby the formation of troublesome byproducts is not encountered.

SUMMARY OF THE INVENTION

Novel antimony mercaptide esters are provided of the formula

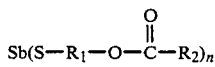
$$Sb(S-R_1-O-\overset{\overset{O}{\|}}{C}-R_2)_n$$

wherein $R_1$ is selected from hydrocarbylene groups having from 2 to 18 carbon atoms, $R_2$ is selected from hydrocarbyl groups having from 1 to 35 carbon atoms and n is 3 or 5.

The term "hydrocarbyl group" is used herein to mean any univalent alkyl, alkenyl, cycloalkyl, cycloalkenyl or aryl group, or any combination of radicals which form univalent groups such as alkaryl, aralkyl, alkenylaryl and the like. The term "hydrocarbylene group" means the same as above except the groups are bivalent.

Methods of preparing the above-described antimony mercaptide esters are also provided. The methods comprise reacting an antimony oxide compound of the formula $Sb_2(O)_n$ with a mercapto alcohol of the formula $HS-R_1-OH$ in a first reaction to form an antimony mercaptide intermediate of the formula $Sb(S-R_1-OH)_n$. The intermediate is then reacted with an organic acid of the formula

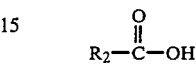
$$R_2-\overset{\overset{O}{\|}}{C}-OH$$

or the anhydride of such acid in a second reaction to form the antimony mercaptide ester.

The second ester forming reaction can be carried out without a catalyst, but the reaction is most preferably carried out in the presence of a titanium catalyst of the formula $Ti(OR_3)_4$ wherein $R_3$ is a hydrocarbyl group having from 3 to 8 carbon atoms.

The first and second reactions described above are advantageously carried out successively in a single reactor, i.e., the first reaction is carried out to form the intermediate product, and then without the isolation of the intermediate product, the ester is formed in the same reactor. The intermediate and ester forming reactions proceed smoothly without the formation of thioxane or other troublesome byproducts.

It is, therefore, a general object of the present invention to provide novel antimony mercaptide esters and methods of preparing such esters.

A further object of the present invention is the provision of methods of preparing novel and useful antimony mercaptide esters in a single reactor without the formation of troublesome byproducts.

Other and further objects, features and advantages of the present invention will be readily apparent to those skilled in the art upon a reading of the description of preferred embodiments which follows.

DESCRIPTION OF PREFERRED EMBODIMENTS

By the present invention novel antimony mercaptide esters are provided having the formula

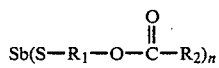
$$Sb(S-R_1-O-\overset{\overset{O}{\|}}{C}-R_2)_n$$

wherein $R_1$ is selected from hydrocarbylene groups having from 2 to 18 carbon atoms, $R_2$ is selected from hydrocarbyl groups having from 1 to 35 carbon atoms and n is 3 or 5.

Preferred such antimony mercaptide esters are those wherein $R_1$ is a hydrocarbylene group having from 2 to 8 carbon atoms. Examples of such groups are ethylene, propylene, butylene, 1,2-cyclohexyl and 2-phenyl ethylene groups. $R_2$ is preferably a hydrocarbyl groups having from 6 to 24 carbon atoms. Examples of such groups are pentyl, hexyl, heptyl, 1-ethylpentyl, nonyl, neo-nonyl and undecyl groups.

Antimony mercaptide esters of the above formula which are particularly preferred are those wherein $R_1$ is an alkylene group, e.g., ethylene, $R_2$ is a branched alkyl group which results in the ester being a liquid, e.g., a 1-ethylpentyl group, and n is 3.

The novel antimony mercaptide esters of this invention have numerous uses such as additives for passivating metals in hydrocarbon catalytic cracking and other similar applications, as anti-foulant additives in ethylene furnaces or the like, as additives for plastics, as fire retardants, etc. The antimony mercaptide esters of the present invention are readily soluble in commonly used hydrocarbon solvents and have low odor making them more suitable for many applications than prior art esters.

The antimony mercaptide esters are prepared by first reacting an antimony oxide compound of the formula $SB_2(O)_n$ with a stoichiometrically equivalent amount of a mercapto alcohol of the formula $HS—R_1—OH$ to form an antimony mercaptide intermediate of the formula $Sb(S—R_1—OH)_n$ wherein $R_1$ is the same as described above and n is 3 or 5. While, as indicated, either antimony trioxide ($Sb_2O_3$) or antimony pentoxide ($Sb_2O_5$) can be used, antimony trioxide is preferred in that it is readily available, and the antimony compounds prepared therefrom have higher antimony content than compounds prepared from antimony pentoxide. The first reaction can be illustrated by the following equation:

$$Sb_2(O)_n + 6HS—R_1+OH \rightarrow 2Sb(S—R_1—OH)_n + H_2O$$

Examples of suitable mercapto alcohols are 2-mercaptoethanol, 2-mercaptopropanol, 2-mercaptobutanol, 1-mercapto-2-hydroxycyclohexane, and 2-phenyl-2-mercaptoethanol. The preparation of such mercapto alcohols and others using methods such as ring opening of the corresponding epoxide with hydrogen sulfide are well known to those skilled in the art. Of the many mercapto alcohols which can be utilized, a presently preferred such alcohol is 2-mercaptoethanol.

The first reaction is carried out at a temperature in the range of from about 25° C. to about 200° C., preferably at a temperature in the range of from about 90° C. to about 100° C. The reaction can be carried out at atmospheric or superatmospheric pressure in air or in an inert atmosphere, e.g., nitrogen, argon, etc.

Examples of the intermediate compound formed in the first reaction are antimony tris(2-hydroxyethylthiolate), antimony tris(2-hydroxypropylthiolate), antimony tris(2-hydroxycyclohexylthiolate), and antimony tris(1-phenyl-2-hydroxyethyl-thiolate).

The intermediate obtained in the first reaction is reacted with a stoichiometrically equivalent amount of an organic acid of the formula

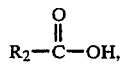

or the anhydride of such acid, in a second reaction to form the antimony mercaptide ester. The $R_2$ group of the organic acid is the same as described above. The reaction can be illustrated by the following equation:

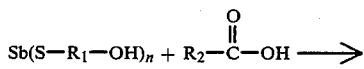

-continued

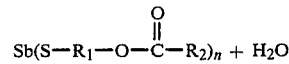

Examples of suitable organic acids which can be utilized include hexanoic acid, heptanoic acid, octanoic acid, 2-ethylhexanoic acid, decanoic acid, neo-decanoic acid, lauric acid, lauroleic acid, myristic acid, myristoleic acid, palmitic acid, palmitoleic acid, stearic acid, isostearic acid, phenylstearic acid, oleic acid, linoleic acid, linolenic acid, and mixtures of fatty acids such as coconut fatty acids, tallow fatty acids, tall oil fatty acids, etc. Of the various organic fatty acids which can be utilized, preferred are hexanoic acid, heptanoic acid, octanoic acid, 2-ethylhexanoic acid, decanoic acid, neo-decanoic acid, dodecanoic acid, oleic acid, stearic acid, and mixtures of such acids. A preferred commercially available fatty acid mixture is tall oil fatty acid sold by Union Camp under the trade name "UNITOL ACD Special" which is comprised of an acid mixture having a typical analysis of about 49.5% by weight oleic acid, 45.1% by weight linoleic acid, 1.6% by weight palmitic and stearic acids, 1.1% by weight miscellaneous acids, 1.0% by weight resin acids and 1.5% by weight unsaponofiables. As noted above, it is within the scope of the present invention to use anhydrides of such organic acids.

The second reaction can be carried out at a temperature in the range of from about 100° C. to about 250° C. with a range of from about 150° C. to about 190° C. being the most preferred. The reaction can be carried out in air or in an inert atmosphere, e.g., nitrogen, argon, etc., at atmospheric or superatmospheric pressure.

While the second reaction can be carried out without a catalyst, the use of a titanium compound catalyst of the formula $Ti(OR_3)_4$ wherein $R_3$ is a hydrocarbyl group having from 3 to 8 carbon atoms is preferred. Examples of such titanium catalysts are methyl titanate, ethyl titanate, n-propyl titanate, isopropyl titanate, tetra-n-butyl titanate, sec-butyl titanate, isobutyl titanate, pentyl titanate, hexyl titanate and octyl titanate. Of the various titanium catalysts which can be utilized, tetra-n-butyl titanate is preferred.

The first intermediate forming reaction and second esterification reaction are advantageously carried out in a single reactor. That is, the first reaction is carried out in a reactor to form the intermediate product, and then without the isolation of the intermediate product, the ester is formed in the same reactor. The removal of water during the course of the reactions is accomplished to drive the reactions to completion. This can be done by sparging with inert gas during the reaction to vaporize the water, carrying out the reaction under reduced pressure, or combining both sparging and pressure reduction during the reaction to vaporize and remove the water. A preferred technique for removing the water is by azeotropic distillation using an azeotropic solvent such as cyclohexane, heptane, octane, benzene, toluene, or xylene. Of the various azeotropic solvents which can be used, toluene and xylene are the most preferred.

At the completion of the second reacton, the product mixture may contain solids from sources such as impurities, inert materials present in the antimony oxide, or hydrolysis products of the titanium catalyst used. All such solids can be easily removed by filtration and the antimony mercaptide ester product can be separated from the azeotropic solvent by vacuum evaporation.

In order to further illustrate the preparation of the novel antimony mercaptide esters of the present invention, the following examples are given.

EXAMPLE 1

This example discloses the preparation of an antimony mercaptide ester of the formula

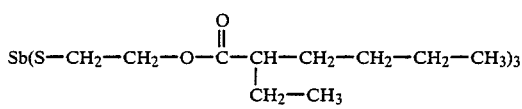

A 1-liter, 3-neck flask reactor equipped with heater, temperature controller, magnetic stirrer and Dean-Stark condenser trap was charged with 156 grams (2.0 moles) of 2-mercaptoethanol and 100 grams (0.33 mole) of antimony trioxide ($Sb_2O_3$). 250 milliliters of xylene were added, and the resulting mixture was heated and refluxed for about 1 hour at temperatures ranging from about 100° C. to about 140° C. whereby 19 milliliters of condensed water were collected in the Dean-Stark trap and the intermediate antimony tris (2-hydroxyethyl thiolate) compound was produced.

288 grams (2 moles) of 2-ethylhexanoic acid were then added to the reaction mixture and heating and refluxing were continued. After about 2 hours, 1 milliliter of tetra-n-butyl titanate catalyst was added. 32 milliliters of condensed water were collected in the Dean-Stark trap over a total time period of about 8 hours during which the temperature ranged from about 165° C. to about 195° C. The resulting liquid mixture was then cooled, vacuum filtered and solvent stripped on a rotary evaporator.

An infrared spectrum of the liquid product showed the disappearance of the free acid C=O band at about 1705 cm$^{-1}$, and the disappearance of the broad —OH band due to both the intermediate —OH and the acid —OH. A new C=O band appeared t 1730 cm$^{-1}$ indicating an ester carbonyl. Elemental analysis of the liquid product showed 16.3% antimony which agreed with the calculated antimony content of 16.6%.

EXAMPLE 2

This example discloses the preparation of an antimony mercaptide ester of the formula

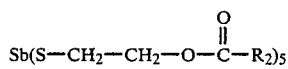

wherein the $R_2$ hydrocarbyl group is provided by a tall oil fatty acid mixture.

A 1-liter, 3-neck flask reactor fitted with a heater, temperature controller, magnetic stirrer and Dean-Stark condenser trap was charged with 79 grams (1 mole) of 2-mercaptoethanol, 32.45 grams (0.1 mole) of antimony pentoxide ($Sb_2O_5$) and 160 milliliters of xylene. The mixture was heated and refluxed for a time period of about 1 hour at a temperature ranging from about 100° C. to about 140° C. whereby 13 milliters of water were collected in the Dean-Stark trap. The resulting reaction mixture containing the intermediate product was cooled to a temperature below the reflux temperature, and 292 grams (1 mole) of tall oil fatty acids were added. The tall oil fatty acids used were those sold under the trade name "UNITOL ACD special" by Union Camp.

The mixture was returned to reflux and after about ¾ hour 6 milliliters of water were collected in the Dean-Stark trap. 1 milliliter of tetra-n-butyl titanate catalyst was added, and after 2 additional hours of heating and refluxing at a temperature ranging from about 164° C. to 166° C., 10 milliliters of water were collected. The resulting product mixture was cooled, filtered and solvent stripped on a rotary evaporator.

An infrared spectrum of the liquid product showed the disappearance of the free acid C=O band at about 1710 cm$^{-1}$ and a new C=O band at 1740 cm$^{-1}$, i.e., the ester carbonyl.

Thus, the present invention is well adapted to attain the ends and advantages mentioned as well as those inherent therein. While numerous changes in reactants, reaction conditions and procedures may suggest themselves to those skilled in the art, such changes are encompassed within the spirit of the invention as defined by the appended claims.

What is claimed is:

1. A method of preparing an antimony mercaptide ester having the formula

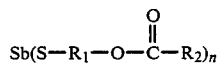

wherein $R_1$ is selected from hydrocarbylene groups having from 2 to 18 carbon atoms, $R_2$ is selected from hydrocarbyl groups having from 1 to 35 carbon atoms and n is 3 or 5 comprising:

reacting an antimony oxide compound of the formula $Sb_2(O)_n$ with a mercapto alcohol of the formula HS—$R_1$—OH in a first reaction to form an antimony mercaptide intermediate of the formula Sb(S—$R_1$-OH)$_n$; and then reacting said intermediate with an organic acid of the formula

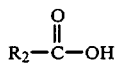

or the anhydride of such acid in a second reaction to form said antimony mercaptide ester.

2. The method of claim 1 wherein said first reaction is carried out at a temperature in he ange of from about 25° C. to about 200° C.

3. The method of claim 1 wherein $R_1$ is a hydrocarbylene group having from 2 to 8 carbon atoms.

4. The method of claim 3 whereifn said mercapto alcohol is selected from the group consisting of 2-mercaptoethanol, 2-mercaptopropanol, 1-mercapto-2-hydroxycyclohexane and 2-phenyl-2-mercaptoethanol.

5. The method of claim 1 wherein said second reaction is carried out at a temperature in the range of from about 100° C. to about 250° C.

6. The method of claim 1 wherein $R_2$ is a hydrocarbyl group having from 6 to 24 carbon atoms.

7. The method of claim 6 wherein said organic acid or the anhydride thereof is selected from the group consisting of hexanoic acid, heptanoic acid, octanoic acid, 2-ethylhexanoic acid, decanoic acid, neo-decanoic acid, dodecanoic acid, oleic acid, stearic acid, and mixtures of the foregoing acids.

8. The method of claim 1 wherein said organic acid or the anhydride thereof is a mixture of acids comprising oleic acid, linoleic acid, palmitic acid and stearic acid.

9. The method of claim 5 wherein said second reaction is carried out in the presence of a titanium compound catalyst of the formula $Ti(OR_3)_4$ wherein $R_3$ is a hydrocarbyl group having from 3 to 8 carbon atoms.

10. The method of claim 9 wherein said titanium compound catalyst is tetra-n-butyl titanate.

11. The method of claim 1 wherein said first and second reactions are carried out successively in a single reactor.

12. The method of claim 11 wherein water is removed from aid reactor during the course of said second reaction.

13. The method of claim 12 wherein said water is removed by azeotropic distillation.

14. A method of preparing an antimony mercaptide ester comprising:
reacting antimony trioxide with a mercapto alcohol of the formula $HS-R_1-OH$ wherein $R_1$ is a hydrocarbylene group having from 2 to 18 carbon atoms in a first reaction to form an antimony mercaptide intermediate; and
reacting said intermediate with a fatty organic acid or the anhydride thereof, said acid being of the formula

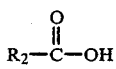

wherein $R_2$ is a hydrocarbyl group having from 1 to 35 carbon atoms in a second reaction to form said antimony mercaptide ester.

15. The method of claim 14 wherein said first reaction is carried out at a temperature in the range of from about 90° C. to about 100° C.

16. The method of claim 15 wherein said second reaction is carried out at a temperature in the range of from about 150° C. to about 190° C.

17. The method of claim 16 wherein said second reaction is carried out in the present of a titanium compound catalyst of the formula $Ti(OR_3)_4$ wherein $R_3$ is a hydrocarbyl group having from 3 to 8 carbon atoms.

18. The method of claim 17 wherein said titanium compound catalyst is tetra-n-butyl titanate.

19. The method of claim 18 wherein said mercapto alcohol is selected from the group consisting of 2-mercaptoethanol, 2-mercaptopropanol, 2-mercapto-1-hydroxycyclohexane and 2-phenyl-2-mercaptoethanol.

20. The method of claim 19 wherein said fatty organic acid or anhydride thereof is selected from the group consisting of hexanoic acid, heptanoic acid, octanoic acid, 2-ethylhexanoic acid, decanoic acid, neodecanoic acid, dodecanoic acid, oleic acid, stearic acid, and mixtures of the foregoing acids.

21. The method of claim 18 wherein said mercapto alcohol is 2-mercaptoethanol.

22. The method of claim 19 wherein said organic acid or anhydride thereof is 2-ethylhexanoic acid.

23. The method of claim 22 wherein said first and second reactions are carried out successively in a single reactor.

24. The method of claim 23 wherein water is removed from said reactor during the course of said second reaction.

25. The method of claim 24 wherein said water is removed by azeotropic distillation.

* * * * *

UNITED STATES PATENT AND TRADEMARK OFFICE
CERTIFICATE OF CORRECTION

PATENT NO. : 4,923,643
DATED : May 8, 1990
INVENTOR(S) : Howard F. Efner

It is certified that error appears in the above-identified patent and that said Letters Patent is hereby corrected as shown below:

Column 2, line 63, delete "groups" and insert --group--.
Column 3, line 30, delete "$Sb_2(O)_n + 6HS-R_1 + OH \rightarrow 2Sb(S-R_1-OH)_n + H_2O$"

and insert --$Sb_2(O)_n + 6HS-R_1-OH \rightarrow 2Sb(S-R_1-OH)_n + H_2O$--.

Column 5, line 41, delete "t" and insert --at--.
Column 6, line 8, before "milliliters" insert --additional--.

Signed and Sealed this

Second Day of July, 1991

Attest:

Attesting Officer

HARRY F. MANBECK, JR.

Commissioner of Patents and Trademarks